US006897041B1

(12) United States Patent
Khatri et al.

(10) Patent No.: US 6,897,041 B1
(45) Date of Patent: May 24, 2005

(54) EXPRESSION OF RECOMBINANT MATURE LYSOSTAPHIN

(75) Inventors: Ghan Shyam Khatri, Delhi (IN); Rahul Sharma, Delhi (IN)

(73) Assignee: Bharat Biotech International Limited (IN)

( * ) Notice: Subject to any disclaimer, the term of this patent is extended or adjusted under 35 U.S.C. 154(b) by 0 days.

(21) Appl. No.: 10/110,795

(22) PCT Filed: Oct. 19, 1999

(86) PCT No.: PCT/IB99/01704

§ 371 (c)(1),
(2), (4) Date: Aug. 22, 2002

(87) PCT Pub. No.: WO01/29201

PCT Pub. Date: Apr. 26, 2001

(51) Int. Cl.[7] .................. C12N 15/00; C12N 15/70; C12N 15/74; C12N 9/52

(52) U.S. Cl. ............... 435/69.1; 435/220; 435/252.3; 435/252.33; 435/320.1

(58) Field of Search ............... 435/69.1, 220, 435/252.3, 252.33, 320.1, 212; 530/350; 536/23.2, 23.7

(56) References Cited

U.S. PATENT DOCUMENTS

| | | | | |
|---|---|---|---|---|
| 4,931,390 A | * | 6/1990 | Recsei .................. | 435/183 |
| 5,079,159 A | * | 1/1992 | Kaufman ............... | 435/226 |
| 5,122,457 A | * | 6/1992 | Reim et al. ............ | 435/69.1 |
| 5,530,100 A | * | 6/1996 | Darling et al. ......... | 530/383 |
| 5,747,321 A | * | 5/1998 | Yabuta et al. .......... | 435/220 |
| 5,830,694 A | * | 11/1998 | Studier et al. ........ | 435/69.1 |
| 6,143,518 A | * | 11/2000 | Cameron et al. ...... | 435/69.1 |
| 6,177,075 B1 | * | 1/2001 | Christian et al. ...... | 424/93.2 |
| 6,361,966 B1 | * | 3/2002 | Walker et al. ......... | 435/69.1 |

FOREIGN PATENT DOCUMENTS

| | | |
|---|---|---|
| EP | 0 759 473 A | 2/1997 |
| WO | WO 87/06264 A1 | 10/1987 |
| WO | WO 99/05289 A1 | 2/1999 |

OTHER PUBLICATIONS

Lazure, C., 2002, "The peptidase zymogen proregions: Nature's way of preventing undesired activation and proteolysis", Current Pharmaceutical Design, vol. 8, pp. 125–133.*

Basak, A., and Lazure, C., 2003, "Synthetic peptides derived from the prosegments of proprotein convertase 1/3 and furin are potent inhibitors of both enzymes", Biochemical Journal, vol. 373, pp. 231–239.*

* cited by examiner

*Primary Examiner*—Ponnathapu Achutamurthy
*Assistant Examiner*—William W. Moore
(74) *Attorney, Agent, or Firm*—Joseph T. Leone, Esq.; DeWitt Ross & Stevens S.C.

(57) ABSTRACT

A portion of the lysostaphin gene of *Staphylococcus simulans* has been cloned and overexpressed in the cytoplasm of *E. coli* to yield lysostaphin, in the absence of preprolysostaphin and prolysostaphin, under the transcriptional control of an IPTG-inducible promoter and a ribosome binding site. IPTG induction of the transformed host cells produces intracellular, soluble, mature lysostaphin (27 kDa), in the complete absence of preprolysostaphin and prolysostaphin. The mature lysostaphin so formed dose not require post-translational modification. The mature lysostaphin so formed can be used treat and prevent *staphylococcal* infections.

22 Claims, 4 Drawing Sheets

Selective PCR Amplification of gene for mature Lysostaphin from the total DNA of S.simulans NRRL B2628

Construction of plasmid pEnd11b for expression of Glycylglycine endopeptidase(Lysostaphin) in E.coli Overexpression of mature lysostaphin endopeptidase in *E.coli* BL21(λDE3)/p*End*11b by IPTG induction Densitometric Scan of 12% SDS PAGE of recombinant lysostaphin expressed in *E.coli* BL21(λDE3)/pEnd11b

SEQUENCE LISTING

<160> NUMBER OF SEQ ID NOS: 2

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: PCR Primer

<400> SEQUENCE: 1
actgaattcc atatggctgc aacacatgaa cattcagcac          40

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: PCR Primer

<400> SEQUENCE: 2
cagatctgga tcctcacttt atagttcccc aaagaacac          39

EXPRESSION OF RECOMBINANT MATURE LYSOSTAPHIN

FIELD OF THE INVENTION

The invention is directed to a method of expressing mature lysostaphin, free from preprolysostaphin and prolysostaphin, in a recombinant bacterial host, vectors encoding mature lysostaphin operationally-linked to inducible promoters, and genetically engineered bacterial hosts which express mature lysostaphin.

DESCRIPTION OF THE PRIOR ART

*Staphylococcal* infections cause a tremendous amount of misery and economic loss to mankind through *staphylococcal* food poisoning, bum and wound infections, and infections of the mammary glands of lactating ruminants. These infections are often resistant to conventional antibiotics or have a tendency to relapse once antibiotics are withdrawn. *Staphylococcus simulans* biovar *staphylolyticus* produces an extracellular zinc metalloprotease glycyl-glycine endopeptidase, known trivially as "lysostaphin," that hydrolyzes the pentaglycine links in cell wall peptidoglycans. Consequently, lysostaphin is active in destroying *Staphylococcal* species but is inactive against all other genera. This unique property of lysostaphin against viable *Staphylococcal* cells provides an antibiotic mechanism which differs strikingly from the mechanism of action of currently used anti-*staphylococcal* antibiotics. As such, lysostaphin offers the possibility of a novel approach to the treatment and prophylaxis of *staphylococcal* diseases. However, the purification of lysostaphin from *Staphylococcus simulans* biovar *staphylolyticus* for detailed physical and biochemical studies, as well as for the valuation of its potential for treating and preventing *staphylococcal* infections remains elusive because of low expression levels and concomitant secretion of potent toxins by the natural source.

The wild-type lysostaphin gene encodes a preproenzyme which consists of three distinct domains with a typical secretion signal peptide of 38 amino acid residues at the N-terminus, followed by a hydrophilic and highly ordered domain of seven tandem repeats of a 13-amino acid sequence, followed by the hydrophobic mature lysostaphin itself, which contains 246 amino acids. The mature enzyme is a monomer of about 27 kDa and contains no disulfide bonds. The conversion of prolysostaphin to mature lysostaphin occurs extracellularly in the culture medium of *S. simulans* and involves the removal of the hydrophilic tandem repeat portion of the proenzyme.

The wild-type gene for lysostaphin endopeptidase (end) is located on a large β-lactamase positive plasmid of *Staphylococcus simulans* biovar *staphylolyticus*. (Heath, L. S., H. E. Heath and G. L. Sloan (1987) "Cloning of the lysostaphin gene of *S. simulans* biovar *staphylolyticus*." *Abstr. Ann. Meet. Am. Soc. Microb.* H58p149; Heath, L. S., H. E. Heath and G. L. Sloan, (1987) "Plasmid encoded lysostaphin endopeptidase gene of *S. simulans* biovar *staphylolyticus*." *FEMS Microb. Lett.* 44:129–133.) The complete operon has been cloned (see Recsei P. A., A. D. Gruss and R. P. Novick (1987) "Cloning, sequence, and expression of the lysostaphin gene from *Staphylococcus simulans*." *Proc. Natl. Acad. Sci. USA* 84:1127–1131; Heinrich P., R. Rosenstein, M. Böhmer, P. Sonner and F. Götz (1987) "The molecular organization of the lysostaphin gene and its sequences repeated in tandem." *Mol. Gen. Genet.* 209:563–569, and U.S. Pat. No. 4,931,390, issued Jun. 5, 1990 to Recsei) and the complete gene was sequenced along with the promoter elements. These references report expression in *E. coli* of preprolysostaphin which is then converted extracellularly into prolysostaphin and lysostaphin. This work was done using the wild-type lysostaphin endopeptidase promoter. Prolysostaphin has also been expressed in a eukaryotic system under the transcriptional control of the cytomegalo virus (CMV) promoter (Williamson C. M., A. J. Bramley and A. J. Lax (1994) "Expression of the lysostaphin gene of *Staphylococcus simulans* in a eukaryotic system." Appl Environ Microbiol; 60(3):771–776.

Earlier methods for production of lysostaphin endopeptidase had been either to purify the enzyme directly from *S. simulans* (Schindler C. A. and V. T. Schuardt (1965) "Purification and properties of lysostaphin: a lytic agent for the *Staphylococcus aureus*." *Biochem. Biophys. Acta.* 97:242–250; Iverson O. J. and A. Grov (1973) "Studies on lysostaphin, separation and characterization of three enzymes." *Eur. J. Biochem.*38:293–300; Valisena S., F. E. Varaldo and G. Satta (1982) "Purification and Characterization of three separate bacteriolytic enzymes excreted by *S. aureus, S. simulans* and *S. saprophyticus*." *J. Bact.* 151:636–647; Sugai M., T. Akiyama, Y. Miyake, E. Ishida and H. Suginaka (1990) "Rapid purification of lysostaphin for analysis of cell-wall proteins." *J. Microb. Meth.* 12:133–138; and Marova I. and V. Dadak (1993) "Modified simplified method for isolation of lysostaphin from the culture filtrate of *Staphylococus staphylolyticus*." *Folia Microbiol.* 38:245–252), or to express prolysostaphin and convert it to mature lysostaphin by cleaving off the propeptide portion using *S. simulans* extract (Marova and Dadak, supra; Williamson et al., supra). Both conventional routes suffer distinct disadvantages. When isolated from the natural source, the mature lysostaphin can be contaminated with pyrogens/allergens and and/or prolysostaphin or preprolysostaphin. When expressed as a proenzyme, the initially expressed prolysostaphin must be enzymatically converted using extracts from the native source to yield the mature lysostaphin. This also provides an opportunity for the lysostaphin to be contaminated with pyrogens or other contaminants.

There are no reports in the prior art describing the cloning and direct expression of the mature form of lysostaphin, absent the expression of a prepro- or pro-form of the protein. Described herein is a method for the direct production of lysostaphin which does not require the intermediate production of a prepro- or prolysostaphin. Consequently, the lysostaphin produced by the subject method is free from pre-prolysostaphin and prolysostaphin.

SUMMARY OF THE INVENTION

Because further evaluation of the anti-*staphylococcal* potential of lysostaphin depends on the ready availability of large amounts of highly purified lysostaphin from a safe and non-pathogenic source, the subject invention is directed primarily to a recombinant plasmid which drives overexpression of mature lysostaphin in the cytoplasm of host cells, preferably *E. coli* cells, transformed to contain the recombinant plasmid.

The invention further encompasses host cells transformed to contain and express the plasmid (preferably transformed *E. coli* cells), a method of producing mature lysostaphin using suitable hosts transformed with the plasmid, and the preprolysostaphin-free and prolysostaphin-free lysostaphin produced by the transformed cell. The recombinant lysostaphin produced according to the present invention has been purified to homogeneity using a procedure involving two chromatographic steps, described herein below. The recombinant product has been characterized for its biochemical, enzymatic, and biophysical properties in order to develop suitable quality control assays of the recombinant product.

Specifically, a first embodiment of the invention is drawn to a method of producing mature lysostaphin endopeptidase free from preprolysostaphin and prolysostaphin. The invention is characterized by providing a genetic construct comprising a nucleotide sequence encoding mature lysostaphin endopeptidase in the absence of prepro and prolysostaphin-encoding elements, and a promoter operationally-linked to the nucleotide sequence encoding the mature lysostaphin endopeptidase; transforming a host cell to contain and express the genetic construct such that mature lysostaphin, free from preprolysostaphin and prolysostaphin, accumulates in the cytoplasm of the host; and then isolating the mature lysostaphin from the host cell.

A second embodiment of the invention is directed to an expression construct for transforming a host to express mature lysostaphin endopeptidase free from preprolysostaphin and prolysostaphin, the construct comprising: a nucleotide sequence encoding mature lysostaphin endopeptidase in the absence of prolysostaphin-encoding elements; and a promoter operationally-linked to the nucleotide sequence encoding the mature lysostaphin endopeptidase.

A third embodiment of the invention is a genetically-engineered host cell transformed with the expression construct described herein such that the transformed cell expresses mature lysostaphin free from contamination with preprolysostaphin or prolysostaphin.

A fourth embodiment of the invention is directed to compositions containing pure lysostaphin, free from preprolysostaphin and prolysostaphin, the compostion produced according to the method described herein.

DETAILED DESCRIPTION OF THE INVENTION

Figure 1:
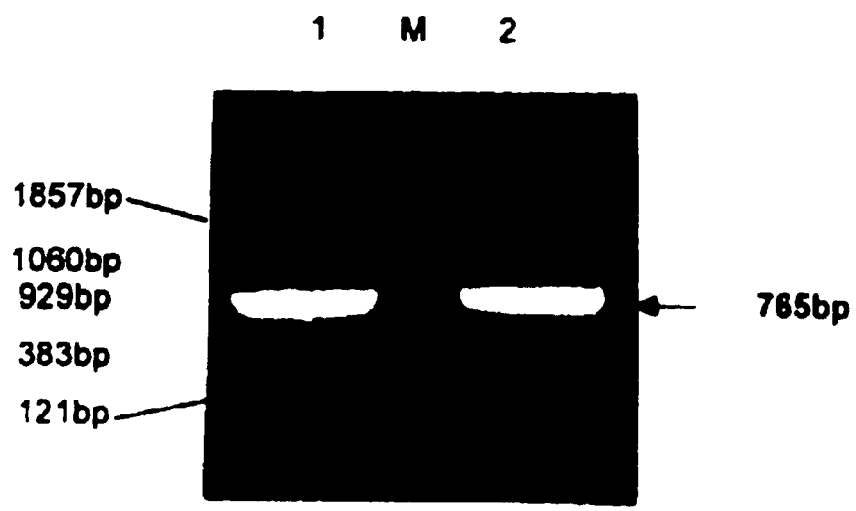
FIG. 1 is an electrophoresis gel showing the amplified lysostaphin gene minus the secretion signal and the 5' repeated motif.

Definitions:

To provide a clear and consistent understanding of the specification, the following definitions are used herein.

Construct or Expression Construct—A DNA construct containing at least one sub-sequence encoding a protein of interest which is operationally linked to one or more regulatory sub-sequences which drive expression of the encoded protein when the construct is transformed into a suitable host cell. Such constructs may also contain subsequences encoding means for selecting host cells transformed to contain the construct, such as sub-sequences which confer antibiotic resistance or dietary limitations to transformed cells, multiple cloning sites, and the like.

Operationally-Linked—When referring to joined DNA sequences, "operationally-linked" denotes that the sequences are in the same reading frame and upstream regulatory sequences will perform as such in relation to downstream structural sequences. DNA sequences which are operationally linked are not necessarily physically linked directly to one another but may be separated by intervening nucleotides which do not interfere with the operational relationship of the linked sequences.

Polymerase Chain Reaction (PCR)—A technique in which cycles of denaturation, annealing with a primer pair, and extension with DNA polymerase are used to generate a large number of copies of a desired polynucleotide sequence. See U.S. Pat. Nos. 4,683,195 and 4,683,202 for a description of the reaction. The PCR is widely used in manipulation of nucleic acids.

Promoter—The DNA sequence site where RNA polymerase binds to the beginning of an operon. Once bound, the RNA polymerase travels along the DNA in the 5' to 3' direction and assembles the corresponding RNA sequences. While the promoter functions as the start signal for RNA synthesis, the promoter itself is not transcribed.

Genetic Engineering:

Many of the steps noted below for the manipulation of DNA, including digesting with restriction endonucleases, amplifying by PCR, hybridizing, ligating, separating and isolating by gel electrophoresis, transforming cells with heterologous DNA, selecting successful transformants, and the like, are well known and widely practiced by those skilled in the art and are not extensively elaborated upon herein. Unless otherwise noted, the DNA protocols utilized herein are described extensively in Sambrook, J., E. F. Fritsch, and T. Maniatis, (1989), "Molecular Cloning: A Laboratory Manual," Cold Spring Harbor Laboratory Press: New York, N.Y.

Host Cells:

The recombinant DNA described herein is incorporated into a host microbe to drive the production of mature lysostaphin free from preprolyostaphin and prolysostaphin. The host microbe may be any bacterial or eukaryotic host amenable to transformation. The preferred host is *E. coli*. For purposes of brevity and clarity only, the following disclosure is limited to a description of *E. coli* transformants. *E coli* is the preferred microorganism because of its ubiquity in both academia and industry, its rapid growth rate, its well-understood and easily manipulable genetics, and the existence of the complete genomic sequence for the organism. However, the invention functions with equal success in other prokaryotic microorganisms, such as *Bacillus subtilis* and the like, as well as in eukaryotes such as yeast. Consequently, the following discussion in no way limits the present invention to its exemplified embodiment in *E. coli*.

Construction of Plasmids:

PCR primers to amplify selectively the gene for mature lysostaphin were designed based on the published lysostaphin endopeptidase (end) sequence (see Recsie et al., supra) and selective amplification of the end gene was carried out by PCR using total DNA of *S. simulans* biovar staphylolyticus NRRL B-2628 (Agricultural Research Service Culture Collection, formerly Northern Regional Research Laboratory, National Center for Agricultural Utilization Research, 1815 North University St., Peoria, Ill. 61604-3999, USA). The coding sequence for the signal peptide and propeptide of lysostaphin were then replaced by an initiator methionine codon (ATG), just before the start of mature lysostaphin (AATHE) by PCR-mediated site-directed mutagenesis. Restriction endonuclease sites for NdeI and BamHI were incorporated at the 5' and 3' end of the modified gene respectively for cloning purposes. A proof-reading thermostable enzyme "VENT" DNA polymerase (New England Biolabs, Beverly, Mass., USA) was used. The modified gene for mature lysostaphin endopeptidase was successfully amplified as evidenced by the PCR product, detected as a single band of 765 bp size in ethidium bromide stained agarose gel electrophoresis (FIG. 1).

Figure 2:
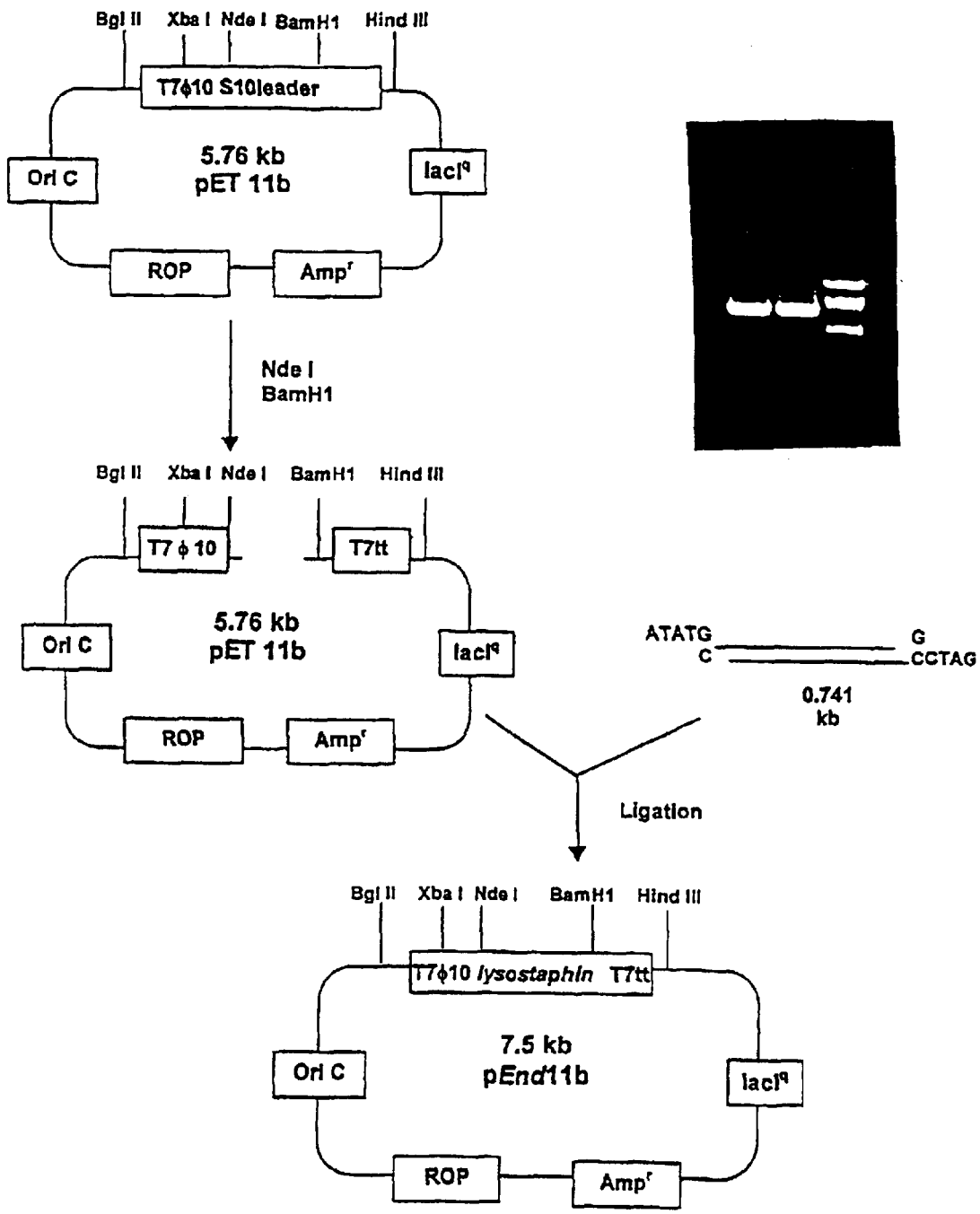
FIG. 2 is a schematic representation of the construction of pEnd-11b, a plasmid construct according to the present invention.

The amplified mature lysostaphin is then operationally-linked to a promoter sequence, preferably an inducible promoter sequence. As shown in FIG. 2, which is described in more detail below, the preferred T7Ø10 inducible promoter is the bacteriophage promoter operationally-linked to the repressor gene lacI$^q$.

The PCR product was digested with NdeI and BamHI restriction enzymes, and the open reading frame was inserted into the pET-11b expression vector (Stratagene, LaJolla, Calif., USA), between NdeI and BamHI sites, thus, placing the gene for mature lysostaphin endopeptidase ORF under the transcriptional control of the strong and regulatable bacteriophage T7Ø10 promoter (see FIG. 2).

The recombinant construct was verified by automated dideoxy chain termination method of DNA sequencing on an ABI Prism 377 Automated DNA Sequencer using dye terminator chemistry. The nucleotide sequence obtained was in complete agreement with the known sequence enconding mature lysostaphin.

Figure 3:
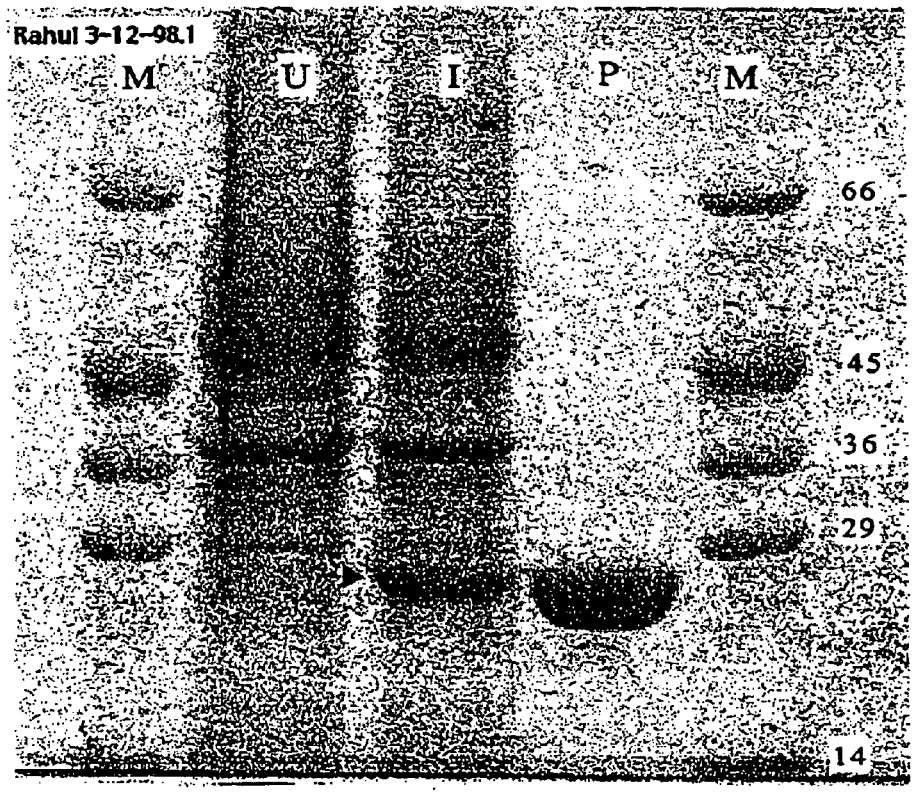
FIG. 3 is an electrophoresis gel of total protein in lysed *E. coli* cells transformed to contain pEnd-11b before and after induction.
Figure 4:
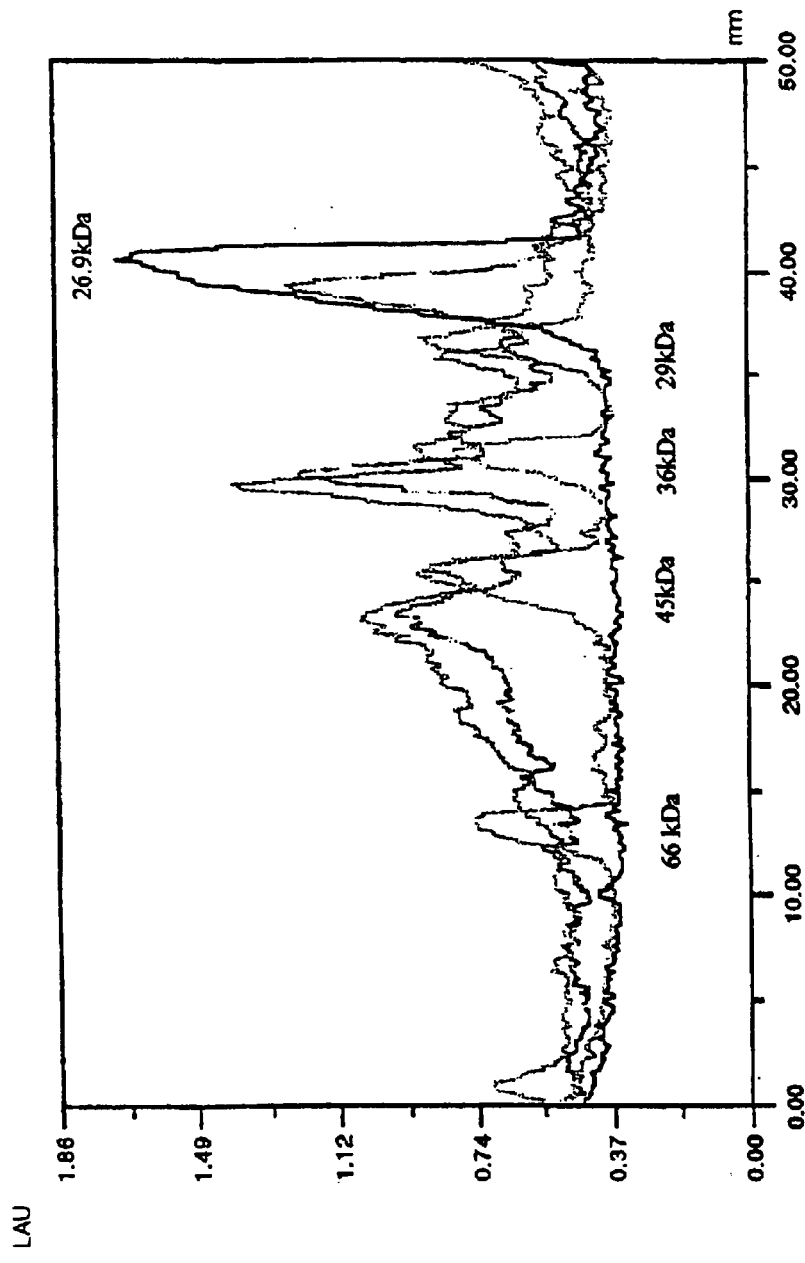
FIG. 4 is a densitometric scan of a 12% SDS-PAGE gel showing the expression level of recombinant mature lysostaphin in *E. coli* transformed to contain pEnd-11b.

Expression of Mature Lysostaphin:

The gene for mature lysostaphin was expressed under the transcriptional control of T7Ø10 promoter in the cytoplasm of *E. coli* BL21(DE3), ATCC 47092 (American Type Culture Collection, 10801 University Boulevard, Manassas, Va. 20110-2209, USA). The recombinant plasmid, designated pEnd-11b, was transformed by conventional means (calcium chloride method) into the preferred host cells, *E. coli* BL21 (DE3). Addition of isopropyl-1-thio-βD-galactoside (IPTG) to a final concentration of 0.4 mM induced th overexpression of a band of approximately 27 kDa molecular weight corresponding to the met-lysostaphin protein. The size of the induced band, as analyzed by SDS-PAGE (see FIG. 3), was in complete agreement with the molecular weight of mature lysostaphin as reported earlier. A densitometric scan of the 12% SDS-PAGE showed that the induced band constituted approximately 20.2% of the total proteins of the induced cell extract (see FIG. 4).

Staphylolytic activity was localized in the same 27 kDa band, visualized as a zone of clearance, due to lysis of *Staphylococcal aureus* cells incorporated in the polyacrylamide gel. The lysostaphin endopeptidase formed according to the above protocol regains its activity even after boiling in SDS and 2-mercaptoethanol, which is concordant with earlier reports (Leclerc D. and A. Asselin (1989) "Detection of cell wall hydrolases after denaturing polyacrylamide electrophoresis." *Can. J. Microb.* 35:749–753).

Purification of Recombinant Lysostaphin Endopeptidase:

The sequence of met-lysostaphin endopeptidase as translated from the nucleotide sequence of the insert in pEnd-11b was analyzed by the computer program DNASTAR (DNASTAR, Inc., Madison, Wis., USA). The data obtained was helpful in designing an efficient scheme to purify the protein. The net charge of met-lysostaphin endopeptidase, as estimated from a titration curve at neutral pH, was found to be +11.39, which clearly indicates that met-lysostaphin is a basic protein having 8.91% (by frequency)/11.04% (by weight) of basic residues. At pH 8.5, which was used for anion exchange chromatography, a large percentage of *E. coli* proteins are adsorbed to Q-Sepharose resin, whereas recombinant lysostaphin endopeptidase appeared in the eluant at 100 mM salt concentration.

The pooled positive fractions were then dialyzed against a pH 5.5 buffer solution, at which point a number of host (*E. coli*) proteins were denatured and precipitated from solution, thereby leaving a very pure preparation of lysostaphin in solution. At pH 5.5, mature lysostaphin, which is a highly basic protein, has a net charge of +18.6. This high net positive charge helps in removal of minor contaminants from the lysostaphin endopeptidase preparation using cation exchange chromatography. The fractions containing pure protein were dialyzed against storage buffer and stored in aliquots at −20° C.

In prior art approaches, lysostaphin has been purified using ammonium sulfate precipitation and DEAE-cellulose chromatography with a yield of 4.3 mg/liter of culture (Schindler and Schuardt, supra). There has also been reported a number of methods to purify lysostaphin from the culture filtrate of *S. simulans* using ion-exchange chromatography (see Iversen and Grov, supra) or a combination of isoelectric focusing and G-100 gel filtration (see Wadstrom T. and O. Vesterberg (1971) "Studies on endo-beta-acetylglucosaminidase, staphylolytic peptidase, and N-acetylmuramyl-L-alanineamidase in lysostaphin and from *S. aureus.*" *Acta Pathol. Microbiol. Scand.* 79:248–264). Purification of lysostaphin based on affinity purification on chitin-sepharose CL4B has also been reported by Valisena et al., supra). Sugai et al., supra, report a process involving dye-ligand affinity high pressure liquid chromatography on Cibacron Blue 3G-A (Tskgel Blue-SPW). However, it has been reported that Cibacron Blue is detrimental for lysostaphin activity (Marova and Dadak, supra).

Marova and Dadak also report a purification protocol for isolation of lysostaphin from culture filtrate of *S. staphylolyticus*, which gave a yield of 75.6% using a series of techniques including ultrafiltration, DEAE-cellulose chromatography, and gel filtration chromatography on Sephadex G-50. The drawback of this protocol is its reliance on three different chromatographic steps, including gel filtration chromatography, which is a cumbersome and time-consuming process.

The production process used herein gives yields of 8.9 mg of purified mature lysostaphin of substantially homogenous purity per liter of laboratory shake flask culture (see the Table in the Examples). There was an achievement of overall 11-fold purification of lysostaphin endopeptidase with good staphylolytic activity (specific activity of 11960 U/mg, which is comparable to the mature lysostaphin supplied by Sigma, St. Louis, Mo., USA). The recovery rate for lysostaphin produced according to the present invention was 70%. The purity of the preparation was near homogeneous as visible on a 12% SDS-PAGE gel stained with coomassie blue.

The subject invention therefore enables the production of recombinant, substantially homogeneous lysostaphin endopeptidase in a safe, non-pathogenic host. The process can be practiced on a laboratory scale or scaled-up to industrial level production.

Biochemical and Enzymatic Characterization of Recombinant Lysostaphin Endopeptidase Produced According to the Invention:

The experimental value obtained from isoelectric focussing in polyacrylamide gel electrophoresis using ampholines was 9.8, which was in accordance with that reported in the literature for native mature lysostaphin. The subunit molecular weight of recombinant lysostaphin endopeptidase calculated from the plot of mobility (Rf) versus log molecular weight of standards, was found to be 26.9 kDa. This value is very close to the theoretically estimated value of 27.2 kDa and to that reported in the literature cited hereinabove.

The molecular weight of the recombinant lysostaphin produced using the present invention, using "Sephacryl S-200" (Pharmacia LKB Biotechnology, Uppsala, Sweden) gel filtration chromatography, was found to be approximately 27 kDa and in complete agreement for mature lysostaphin obtained from *S. simulans* culture filtrate. The rate of lysostaphin activity for the protein produced according to the present invention was linear from 1 to 10 minutes and the specific activity was found to be comparable to commercial lysostaphin (Sigma) under Sigma's specified conditions. The recombinant mature lysostaphin endopeptidase was found to be most active at about 47° C. and a pH range of from about 7.0 to about 9.0 (with a peak value at about 8.0). Notably, however, the protein preparation made according to the present invention retained about 82% of its activity at a pH of about 10.0. When incubated at different temperatures for different time intervals, it was found that the protein preparation according to the invention was stable up to about 50° C. for about 10 minutes of incubation time, beyond which parameters the protein rapidly lost its stability (for example, the protein retained only about 40% activity after 10 minutes heat treatment at 60° C.). At 20° C. and 30° C., the recombinant lysostaphin was stable for at least 24 hours. At 40° C., the recombinant lysostaphin was quite stable for 4 hours, retaining 70% residual activity. The properties of recombinant lysostaphin obtained using the subject invention differed with the earlier reports of Schindler and Schuardt, Recsei et al., and Iverson and Grov, supra, in that the reported optimum temperature and pH were reported as 37° C. and 7.5, respectively. In contrast, the lysostaphin produced according to the present invention has optimum activity at about 47° C. and about pH 8.0.

EXAMPLES

The following Examples are included solely to aid in a more complete understanding of the invention described and claimed herein. The Examples do not limit the scope of the claimed invention in any fashion.

Construction of Recombinant Expression Vector:

Referring now to FIG. 2, the secretion signal peptide and the tandem repeats representing the propeptide were replaced by an ATG initiation codon accompanied by creation of EcoRI restriction site at the 5' end, and a BamHI restriction site immediately following the termination codon of the structural gene for lysostaphin by PCR-mediated site-directed mutagenesis using the primers:

5'-ACTG AATTCCATATGGCTGCAACACATGAACATTCAGCAC-3' (SEQ. ID. NO: 1) (underlined is Nde I restriction site); and 5'-CAGATCT GGATCCTCACTTTATAGTTCCCCAAAGAACAC-3' (SEQ. ID. NO: 2) (underlined is BamH1 restriction site).

The modified gene was selectively amplified from the plasmid pRJ5 (Recsei et al, supra, ATCC 67079) by PCR in a standard reaction using "VENT" DNA polymerase (New England Biolabs), which has a 3' to 5' exonuclease proofreading activity in a Perkin-Elmer C tus thermal cycler. The amplification conditions were 25 cycles of 94° C. for 1 minute, 65° C. for 1 minute, and 72° C. for 40 seconds. The amplified fragment is depicted in FIG. 1, wherein M is a lane of molecular weight markers and lanes 1 and 2 are duplicate amplifications 5 showing the 765 base pair amplification product.

The amplified mature lysostaphin gene, minus the secretion signals and tandem repeats, but operationally-linked to the ATG initiation codon, was then ligated to a sequence encoding the lacI$^q$ repressor and bacteriophage T7Ø10 promoter, to yield a construct in which the mature lysostaphin gene having a 5' ATG start codon was operationlly-linked to the lacI$^q$ repressor and IPTG-inducible T7Ø10 promoter. The lacI$^q$ and promoter sequences can be had from readily available vectors such as pET-11b.

The construct containing the mature lysostaphin operationally-linked to the promoter was digested with NdeI and BamHI restriction endonucleases and inserted into a correspondingly digested pET-11b expression vector to generate the recombinant plasmid pEnd-11b, with the lysostaphin gene under the transcriptional control of T7Ø10 promoters.

Cytoplasmic Expression of Mature Lysostaphin and Localization of Staphylolytic Activity:

The expression host *E. coli* BL21 (DE3) was transformed with pEnd-11 b. Two hundred microliters of overnight grown culture of *E coli* BL21(DE3)(pEnd-11b) was inoculated into 25 ml of Luria Bertani Broth containing 50 μg/ml ampicillin. The culture was grown at 37° C. with vigorous shaking to an optical density of 0.6 (A600 nm) and then IPTG 0.4 mM was addad to induce expression of the mature lysostaphin in the cytoplasm of *E. coli*. Three hours post induction the cells were pelleted by centrifugation, resuspended in 2.5 ml of 50 mM Tris-HCl, broken by ultrasonication and centrifuged to remove the particulate fraction. The total cell extract, and the soluble fraction were analyzed on a 12% SDS-PAGE gel and stained with coomassie brilliant blue following known protocols (Laemmli U. K. (1970) "Cleavage of structural proteins during assembly of head of bacteriophag T4." *Nature* 227:680–685). The 12% SDS-PAGE was analyzed to determine the expression level of recombinant protein by gel densitometry using a FUJI GELSCAN densitometer. The results, shown in FIG. 4, revealed that the expressed mature lysostaphin accounted for 20.2% of cytoplasmic protein.

Localization of Staphylolytic Activity:

The staphylolytic activity band was localized in 12% SDS-PAGE gels using the method described by Sugai et al. (1990), supra, with slight modification. The buffer system used for electrophoresis was the same as reported by Laemmli (1970), supra. Briefly, 12% SDS-polyacrylamide gel was prepared containing 1% (w/v wet cell mass) *S. aureus* 237 cells. Electrophoresis was carried out at 4° C. at 20 mA constant current using a BIORAD Miniprotean vertical slab gel electrophoresis assembly. Following electrophoresis, the gel was washed thoroughly with cold distilled water (3×100 ml). A final soak of 30 minutes at 37° C. was given in 50 mM Tris-HCl, pH 8.0 containing 100 mM NaCl. The activity bands were visualized in a dark background in an indirect light.

Purification of Mature Lysostaphin:

Two-liters of LB broth containing 50 mg/ml ampicillin were inoculated with 10 ml of overnight grown transformant culture of *E coli* BL21 (DE3)(pEnd-11b) and grown at 37° C. with constant agitation (200 rpm) to an optical density of 0.6(A600 nm) and then induced by adding IPTG to a final conc. of 0.4 mM. Post-induction cells were allowed to grow for another 3 hours at 42° C. The induced cells were then centrifuged at 8000 rpm for 10 minutes in a Sorvall GS-3 rotor at 4° C. and resuspended in 100 ml lysis buffer (50 mM Tris-HCl, pH 8.5, containing 100 mM NaCl and 0.5 mM phenylmethylsulfonyl fluoride).

Step I: Anion Exchange Chromatography:

A glass column was packed with 70 ml of anion exchange resin "Q-sepharose FF" (Pharmacia) and equilibrated with 100 ml of lysis buffer. The flow rate was maintained at 2 ml/min. The protein solution was applied to the column and the eluant was collected in fraction volumes of 100 ml each. The column was then washed with 100 ml of the same buffer and the fractions were collected as before. The peak fractions were analyzed by SDS-PAGE and for staphylolytic activity, as described above.

Step II: Acidification and Cation Exchange Chromatography:

The fractions containing lysostaphin were pooled and dialyzed against 20 volumes of cation exchange buffer (40 mM Tris-acetate pH 5.5, 100 mM NaCl) at 4° C. for 16 hrs. The dialysate was centrifuged at 15000 rpm for 15 minutes at 4° C. and the clarified supernatant was used for cation exchange chromatography. A 20 ml capacity glass column was packed with S-sepharose FF (Pharmacia) and equilibrated with 40 ml of cation exchange buffer. A flow rate of 2 ml per minute was maintained throughout the chromatography.

The clarified supernatant from above was loaded onto the equilibrated column and the column was washed with 5 bed volumes (100 ml) of the same buffer followed by a 5 bed volume wash with the same buffer containing 150 mM NaCl. The lysostaphin bound to the matrix was eluted using a 100 ml gradient of 150 mM NaCl to 500 mM NaCl in cation exchange buffer. Fractions of 5 ml volumes were collected and analyzed for the presence of mature lysostaphin endopeptidase by SDS-PAGE and staphylolytic activity. The fractions containing pure recombinant protein were pooled and the homogenous preparation was dialyzed against 10 volumes of storage buffer (50 mM Tris-HCl, pH 7.5, 100 mM NaCl, 50% (v/v) glycerol) before storing at −20° C. Yield was 8.9 mg/ml. See the following Table for step-by-step yield and activity data:

| Purification Step | Total Volume (ml) | Total Prot in (mg) | Activity U/mg | Yield (%) | Purification (fold) |
|---|---|---|---|---|---|
| Cell Extract (Sonicated) | 100 | 280 | 1086 | 100 | — |
| Soluble Fraction | 100 | 232 | 1250 | 96 | 1.15 |
| Anion Exchange | 170 | 55.25 | 5169 | 94 | 4.76 |
| Acidification | 174 | 43.50 | 5540 | 78 | 5.61 |
| Cation Exchange | 37 | 17.80 | 11960 | 70 | 11.10 |

Assay Of Lysostaphin Activity:

Lysostaphin endopeptidase activity was assayed in solution by monitoring the lysis of Staphylococcus aureus 237 cells by the modification of a reported method (Robinson, J. M., J. K. Hardman and G. L. Sloan (1979) "Relationship between lysostaphin endopeptidase production and cell wall composition in Staphylococcus staphylolyticus." J. Bact. 137:1158–1164). Briefly, actively growing cells of S. aureus 237 were rinsed, suspended in activity buffer (50 mM Tris-HCl, pH 7.5, 100 mM NaCl) and optical density (A600 nm) was adjusted to 0.400. The typical assay was arranged in a 3.0 ml quartz cuvette with a 1 cm path length in a Shimadzu 2101 spectrophotometer having an "in situ" controlled temperature cuvette holder maintained at 37° C. An aliquot of appropriately diluted recombinant lysostaphin solution was added to the suspension and the decrease in the OD of cells at 600 nm after a 5 minute incubation period at 37° C. was recorded. One Unit of lysostaphin was defined as the amount of enzyme required to decrease the OD (A600 nm) of a suspension of S. aureus 237 cells by 0.001 at 37° C. in 5 minutes in a 3 ml reaction volume. The purified lysostaphin made according to the present invention has an activity of 11960 U/mg.

What is claimed is:

1. A method of producing mature lysostaphin endopeptidase free from preprolysostaphin and prolysostaphin, the method comprising:

(a) providing a genetic construct comprising a nucleotide sequence encoding mature lysostaphin endopeptidase comprising an initiation codon at its 5'-terminus in the absence of prolysostaphin-encoding elements, wherein the nucleotide sequence encoding the mature lysostaphin endopeptidase is operationally linked at its 5' end to a promoter;

(b) transforming a host cell to contain and express the genetic construct of step (a), such that mature lysostaphin, free from preprolysostaphin and prolysostaphin, accumulates in the cytoplasm of the host; and (c) isolating the mature lysostaphin from the host cell.

2. The method of claim 1, wherein step (a) comprises providing a construct comprising an inducible promoter.

3. The method of claim 1 or claim 2, wherein step (a) comprises providing a construct comprising an IPTG-inducible promoter.

4. The method of claim 1 or claim 2, wherein step (a) comprises providing a construct comprising bacteriophage T7Ø10 promoter.

5. The method of claim 1 or claim 2, wherein step (a) comprises providing a construct further comprising a repressor operationally-linked to the promoter.

6. The method of claim 5, wherein step (a) comprises providing a construct further comprising a lacI$^q$ repressor gene.

7. The method of claim 1, wherein in step (b) comprises transforming E. coli.

8. A method of producing mature lysostaphin endopeptidase free from preprolysostaphin and prolysostaphin the method comprising:

(a) providing a genetic construct comprising a nucleotide sequence encoding mature lysostaphin endopeptidase in the absence of prolysostaphin-encoding elements, and a promoter operationally-linked to the nucleotide sequence encoding the mature lysostaphin endopeptidase;

(b) transforming a host cell to contain and express the genetic construct of step (a), such that mature lysostaphin, free from preprolysostaphin and prolysostaphin, accumulates in the cytoplasm of the host; and (c) isolating the mature lysostaphin from the host cell, wherein step (c), comprises isolating the mature lysostaphin by:

i) lysing the host cells to yield a lysate;

ii) passing the lysate over an anion exchange resin and collecting and pooling fractions exhibiting staphylolytic activity;

iii) acidifying the pooled fractions of step ii) and passing the acidified pooled fractions over a cation exchange resin and collecting and pooling fractions exhibiting staphylolytic activity.

9. The method of claim 8, wherein step (a) comprises providing a construct comprising a nucleotide sequence encoding mature lysostaphin endopeptidase in the absence of prolysostaphin-encoding elements, operationally-linked at its 5' terminus to a start codon, operationally linked at its 5' end to an inducible promoter.

10. The method of claim 8, wherein step (a) comprises providing a construct comprising an IPTG-inducible promoter.

11. The method of claim 8, wherein step (a) comprises providing a construct comprising bacteriophage T7Ø10 promoter.

12. The method of claim 8, wherein step (a) comprises providing a construct further comprising a repressor operationally-linked to the promoter.

13. The method of claim 12, wherein step (a) comprises providing a construct further comprising a lacI$^q$ repressor gene.

14. The method of claim 8, wherein step (b), comprises transforming E. coli.

15. An expression construct for transforming a host to express mature lysostaphin endopeptidase free from preprolysostaphin and prolysostaphin, the construct comprising a nucleotide sequence encoding mature lysostaphin endopeptidase comprising an initiation codon at its 5'-terminus in the absence of prolysostaphin-encoding elements, wherein the nucleotide sequence encoding the mature lysostaphin endopeptidase is operationally linked at its 5' end to a promoter.

16. The construct of claim 15, wherein the expression construct comprises an inducible promoter.

17. The construct of claim 9 or claim 16, wherein the promoter is an IPTG- inducible promoter.

18. The construct according to claim 15 or claim 16, wherein the promoter is bacteriophage T7Ø10 promoter.

19. The construct of claim 15 or claim 16, wherein the construct further comprises a repressor operationally-linked to the promoter.

20. The construct of claim 19, wherein the repressor is a lacI$^q$ repressor gene.

21. A genetically-engineered host cell comprising a host cell transfomed to contain a construct according to any one of claim 15 or 16, wherein the genetically-engineered host cell so transformed expresses mature lysostaphin endopeptidease free from preprolysostaphin and prolysostaphin in its cytoplasm.

22. The genetically-engineered host cell of claim 21, wherein the host cell is E. coli.

* * * * *